United States Patent [19]

Prudden

[11] 4,444,752
[45] Apr. 24, 1984

[54] METHOD FOR TREATING PROGRESSIVE SYSTEMIC SCLEROSIS

[75] Inventor: John F. Prudden, Upper Nyack, N.Y.

[73] Assignee: Lescarden Ltd., New York, N.Y.

[21] Appl. No.: 417,493

[22] Filed: Sep. 13, 1982

[51] Int. Cl.³ .................. A61K 35/60; A61K 35/32; A61K 35/56
[52] U.S. Cl. .................................................. 424/95
[58] Field of Search .......................................... 424/95

[56] References Cited

U.S. PATENT DOCUMENTS 3,400,199  9/1968  Balassa ................................. 424/95
3,966,908  6/1976  Balassa ................................. 424/95

Primary Examiner—Sam Rosen
Attorney, Agent, or Firm—Darby & Darby

[57] ABSTRACT

Disclosed herein is a method for the treatment of progressive systemic sclerosis by the oral administration of a pharmaceutical formulation containing finely divided cartilage powder.

14 Claims, No Drawings

METHOD FOR TREATING PROGRESSIVE SYSTEMIC SCLEROSIS

BACKGROUND OF THE INVENTION

This invention pertains to a method for the treatment of progressive systemic sclerosis by the oral administration of finely divided animal, fish or reptilian cartilage.

Progressive systemic sclerosis (PSS) is a connective tissue disease that ultimately leads to fibrosis involving the skin (scleroderma) and widely disseminated internal organs including the gastrointestinal tract, lungs, heart, and kidney. A chronic disorder of unknown etiology, PSS is often initially identified by the appearance of tight, firm skin on the patient sometime prior to the apparent involvement of internal organs. In some patients, internal disease can occur in the absence of skin involvement. PSS is more common in women. The terms PSS, scleroderma and dermatosclerosis are used interchangeably to identify this disorder. In the advanced stages of the disease the skin becomes firm, thickened and leathery in appearance and is tightly bound to the underlying subcutaneous tissue. Taughtness of the skin over the fingers, and arms may limit full extension of these organs.

Although many drugs have been used to treat PSS, there is no known cure and no single drug has produced any prolonged consistent therapeutic benefit. An article by Prudden and Balassa in "Seminars in Arthritis and Rheumatism" (Vol. III, No. 4-Summer 1974, pp. 287–321) discloses (pp. 317–319) the administration to a patient afflicted with PSS (of a five percent (5%) solution of a sterile high termperature aqueous cartilage extract) by subcutaneous injection. In this trial the patient received between about 50 and 400 cc of the 5% extract per month. The article reports that some improvement was noted in the patient's skin flexibility and thickness, but does not indicate any significant alleviation of the limited range of motion in certain body appendages that is a common feature of the disease. Also it did not comment on any improvement or effect on gastric-intestinal function or respiratory efficiency, both of which are affected by this systematic malady. The pharmaceutical formulation used by Prudden, et al. in "Seminars in Arthritis and Rheumatism" was prepared by extracting finely divided cartilage powder under high temperature and high pressure in an autoclave. All treatment was given via the parenteral route. The patient received the equivalent of between about 2½ and 20 grams per month of finely divided cartilage powder (in divided doses administered at spaced apart intervals) through the parenteral route. In most instances it was necessary to admit the patient to the hospital to administer the large volumes of liquid medication that were required. The article by Prudden et al suggests that parenteral administration of the active agent in a liquid dosage form is required to facilitate transport of the agent throughout the body.

The treatment disclosed in the preceding article does not lend itself to self-administration by the patient on a long term basis, utilizes a pharmaceutical formulation that is relatively expensive to prepare (due to the need for extraction at high temperature and under high pressure) and is limited to the administration of relatively low quantities (between about 2½ and 20 grams) of active agent per month.

It has now been unexpectedly found that the limited range of joint motion associated with PSS and particularly scleroderma can be treated through the high dose oral administration of finely divided cartilage powder of the type having been previously described in U.S. Pat. No. Re. 28,093.

Accordingly, one aspect of the present invention is to provide a method of treating PSS, scleroderma and related disorders in mammals.

A further aspect of the present invention involves the treatment of PSS in mammals by the oral administration of an effective quantity of a pharmaceutical formuation containing finely divided cartilage powder.

Still another aspect of the present invention is to provide a method of improving joint mobility and alleviating skin tension in mammals afflicted with PSS by the oral administration of at least about five grams per day of finely divided cartilage powder.

These and other objects of the present invention will be apparent upon consideration of the following specification.

As used throughout the specification the term "cartilage product" means finely divided cartilage powder derived from granulated animal, reptile or fish cartilage.

The cartilage products used in the composition of the present invention are old and have been described in U.S. Pat. No. Re. 28,093, the disclosure of which is incorporated herein by reference. The cartilage used to make the cartilage products of this invention are preferably derived from young cartilage, i.e. from young animals or, young or newly regenerated cartilage from older animals as reptiles or from species such as fish or shark in which the cartilage remains permanently young. Where age is the criteria for determining "youth", the cartilage is preferably derived from animals not over six months old. However, cartilage products made from the cartilage of older animals may also be employed, but is somewhat less effective in treating PSS.

The cartilage may be prepared by any suitable means to result in a product which is essentially pure cartilage substantially free from adhering tissue which may have been removed by acid pepsin or other suitable enzyme treatment, with or without mechanical assistance or otherwise.

The cartilage powder material of the present invention is preferably prepared by pulverizing rough granulated cartilage to an average particle size of less than about 150 microns, and preferably less than 70 microns. Any number of techniques including ball milling, hammer milling in an inert atmosphere, pebble milling and fluid energy mill grinding may be used to pulverize the cartilage materials. Further details on the preparation of the cartilage powder products that are useful in the present invention are given in U.S. Pat. No. 3,400,199. The cartilage product of the present invention should be formulated so as to be suitable for oral administration. Preferably, the active ingredient is contained in a solid dosage form such as a capsule beadlet or tablet. However, liquid suspensions, solutions, powders, gels and solutions of cartilage powder formulated for oral administration may also be used successfully. The quantity or effective dose supplied by each dosage unit (e.g. capsule or tablet) is relatively unimportant as the total dosage can be reached by administration of either one or a plurality of capsules or tablets or both. The capsules employed may be formed with any of the well-known pharmaceutically acceptable materials such as gelatin, cellulose derivatives, etc. Tablets may be formulated in accordance with conventional tableting procedures employing solid carriers and lubricants that are well known in the art. Examples of solid carriers that may be used in the present invention include starch, sugar and bentonite.

In the treatment of PSS and scleroderma in particular, the active cartilage agent is orally administered to the patient on a daily basis in relatively high dosages of between about 9 and about 60 grams per day. Preferably, the active agent is adminstered in the form of hard shell capsules or tablets containing between about 50 and 500 milligrams of the active ingredient. An especially preferred form of the invention involves administration of a hard shell dosage form containing 375 milligrams of active ingredient.

For patients suffering from PSS, the active ingredient is preferably administered at a dosage level of between 9 and about 60 grams per day. The total daily dose is preferably administered in divided dosages taken two or three times per day. The precise quantity of active ingredient to be administered to a particular patient according to this invention depends upon the severity of condition, the stage and the individual characteristics of the patient under treatment.

An unexpected benefit of the present invention is the rapid alleviation of skin tautness and increase in joint mobility experienced by patients shortly after initiation of treatment. As the onset of PSS occurs over a relatively long time period, it is especially surprising to achieve relatively rapid reversal of the principal clinical symptoms of the disease. This was particularly unexpected in view of the long gradual onset of the disease.

A further surprising aspect of the present invention is that this rapid reversal of scleroderma symptoms is achieved with a drug administered via the oral route. Especially noteworthy was the increase in range of joint motion experienced by patients receiving the drug (as this improvement is measured with an objective test).

The following examples illustrate the preparation of cartilage materials which are useful as active agents according to the present invention.

EXAMPLE I

Cartilage Pebble Mill-ground

The tracheas of healthy adult beef cattle were removed within 30 to 60 minutes after the animals were slaughtered. The tracheas were then either processed immediately with an acid-pepsin solution or they were frozen to preserve them, in which case the acid-pepsin digestion may be deferred. The tracheas, either fresh or previously frozen, were then digested for about six hours at 50° C. in an aqueous solution containing 0.6% acetic acid (U.S.P. glacial) and 0.3% pepsin (N.F. IX grade, 3500 activity). After digestion the tracheal cartilage was removed from the acid-pepsin solution, washed first with water of about 70° C. and then with water of about 25 C. until the effluent wash water showed no trace of pepsin or acetic acid. The cartilage was dried in vacuum (20 mm. mercury) at 80° C. The dried cartilage was defatted by extracting it with a solvent, such as hexane It was then granulated. The resulting cartilage granules ranged in size from about 250 to about 500 microns.

EXAMPLE II

Cartilage obtained from the tracheas of a one month old calf was obtained by the same procedure as described in Example I and the resulting cartilage was ground to an average particle size of about 500 microns in a laboratory four quart size porcelain jar mill loaded with one inch size (average) flint pebbles in a weight ratio of 1 cartilage to 2 pebbles. Dry ice ($CO_2$) was then put on top of the mill charge. The lid of the mill was then clamped on tight and the mill rotated as is customary in the performance of a grinding operation. The grinding was carried out at about 20° C. for 96 hours. The resulting cartilage granules (approx. 40–200 microns) were thoroughly admixed in aqueous isotonic saline, and the admixture heated in an autoclave at 121° C. for 90 minutes at 15 pounds pressure to complete the extraction. The suspended matter was removed by centrifugation and the resulting tan liquid used to fill 50 ml. vials, and then sterilized in the autoclave at 121° C. for 15 minutes at 15 psi. Cartilage powder may also be obtained from cartilage souces such as pigs, lambs, goats, skeleton of sharks, rodents, crocodiles, birds, fish, etc. Reptile cartilage is particularly desirable in view of the ability of reptiles to regenerate their tissues and even their imbs. More details on obtaining cartilage powder from these and other sources will be found in U.S. Pat. No. Re. 28,093.

EXAMPLE III

Liquid cartilage extracts suitable for oral administration in the treatment of PSS were prepared as follows:

The cartilage obtained from a one day old calf was acid-pepsin digested as in Example I, granulated to an average particle size of about 0.2 cm, and then without drying was suspended in the extracting liquid, isotonic saline solution, and then transferred into a pebble mill which was charged to 50% of its volume with flint pebbles of average size, one inch diameter. The ratio of the cartilage to extracting liquid was kept at 25:75. The liquid suspension was charged into the mill in a quantity just sufficient to fill the voids of the pebbles with the top of the pebbles barely covered by the liquid. The air was then purged from the mill with nitrogen and the mill closed. The mill was allowed to run for 6 hours between 3° C. and 4° C. which resulted in a medium fine grinding of the cartilage granules and in the simultaneous extraction of the active wound-healing agent from the cartilage.

At the end of the 6-hour cycle, the mill was emptied, the fluid paste strained free of the pebbles, the fluid transferred into a centrifuge operated at 6000 r.p.m. and at a temperature of about 3° C. After one-half hour the centrifuge was stopped and the supernatant liquid strained through a 400 mesh nylon screen. If the strained extract was cloudy, ir was returned to the centrifuge and the centrifuging repeated until a clear sightly opalescent extract was obtained.

The extracts were stored at 40 C. preserved with 0.9% benzyl alcohol.

EXAMPLE IV

To evaluate the effectiveness of the treatment of the present invention, two patients afflicted with PSS were treated under clinical conditions. Each patient orally ingested between 9 and 18 grams per day of finely divided cartilage product for a period of approximately six months. The participants in the study were monitored on a clinical basis and their improvement and symptomatic relief studied using conventional objective measurements. After the initial stages of treatment, each patient's daily dosage and the frequency of administration was varied depending upon the individual's response to the drug. The following tabulation reports on the results obtained in these patients with oral cartilage powder therapy.

show that, in general, the patient experienced a significant and progressive improvement in joint mobility as well as skin flexibility. These changes resulted in continuing improvement in daily functional capacity.

TABLE I
RANGE OF MOTION TEST-PASSIVE

| LEFT Date of Examination | | | | | | RIGHT Date of Examination | | | | | |
|---|---|---|---|---|---|---|---|---|---|---|---|
| 6 Mos. | 4 Mos. | 12 Wks. | 6 Wks. | Before Treatment | Motion | Normal Range | Before Treatment | 6 Wks. | 12 Wks. | 4 Mos. | 6 Mos. |
| 172° | 155° | 155° | 155° | 145° | Shoulder Flexion | (0–160) | 120° | 125° | 125° | 130° | 120° |
| 160° | 140° | 140° | 140° | 140° | Abduction | (0–160) | 105° | 105° | 115° | 115° | 95° |
| | | | | | Internal Rotation | (0–90) | 60° | 60° | 60° | 60° | |
| | | | | | External Rotation | (0–90) | 70° | 65° | 65° | 65° | |
| 82° | 70° | 70° | 65° | 65° | Wrist Flexion | (0–90) | 75° | 75° | 75° | 75° | 88° |
| 72° | 65° | 60° | 50° | 45° | Extension | (0–70) | 65° | 65° | 65° | 65° | 80° |
| 50° | 40° | 40° | 40° | 40° | MCP | (0–90) | 40° | 45° | 50° | 50° | 45° |
| 75° | 60° | 60° | 60° | 60° | IP | (0–90) | 55° | 60° | 65° | 65° | 80° |
| 100° | | | | | Second Digit-MCP | (0–90) | | | | | 95° |
| 110° | 95° | 95° | 90° | 90° | PIP | (0–120) | 90° | 90° | 90° | 90° | 95° |
| 45° | 45° | 50° | 45° | 45° | DIP | (0–80) | 40° | 45° | 60° | 60° | 45° |
| 115° | | | | | Third Digit-MCP | (0–90) | | | | | 95° |
| 115° | 100° | 105° | 105° | 105° | PIP | (0–120) | 100° | 100° | 105° | 105° | 100° |
| 50° | 55° | 60° | 55° | 55° | DIP | (0–80) | 40° | 45° | 50° | 50° | 50° |
| 115° | | | | | Fourth Digit-MCP | (0–90) | | | | | 115° |
| 120° | 110° | 110° | 110° | 110° | PIP | (0–120) | 110° | 100° | 110° | 100° | 118° |
| 75° | 65° | 65° | 55° | 55° | DIP | (0–80) | 45° | 55° | 60° | 60° | 65° |
| 115° | | | | | Fifth Digit-MCP | (0–90) | | | | | 120° |
| 115° | 105° | 105° | 105° | 105° | PIP | (0–120) | 105° | 100° | 105° | 105° | 112° |
| 90° | 90° | 90° | 85° | 80° | DIP | (0–80) | 60° | 85° | 90° | 90° | 90° |
| | | | | | MCP Extension | (90–0) | | | | | |
| | −15° | −10° | −15° | −15° | Index | | −25° | −20° | −15° | −20° | |
| | −10° | −10° | −15° | −15° | Middle | | −30° | −25° | −20° | −20° | |
| | −5° | 0° | −5° | −15° | Ring | | −15° | −15° | −5° | −5° | |
| | −5° | 0° | −5° | −15° | Little Finger | | −15° | −10° | 0° | 0° | |
| | | | | | Tips of Fingers to Palm Crease | | | | | | |
| | 3.5 cm | 3.5 cm | 3.5 cm | 4 cm | Index | | 4 cm | 3 cm | 3.5 cm | 3 cm | |
| | 2 cm | 1.5 cm | 2 cm | 2 cm | Middle | | 2 cm | 2 cm | 2 cm | 2 cm | |
| | 1 cm | 1 cm | 1.5 cm | 1.5 cm | Ring | | 1.5 cm | | | | |

Patient No. 1—51 year old female

Dosage: 9 grams per day of powdered cartilage material (3.75 gms in gelatin capsules) (prepared according to Example II) herein for six months.

General description and diagnosis: This patient was afflicted with severe scleroderma. On examination prior to initial treatment the patient displayed limited ability for joint movement in the shoulder, elbow and wrist. The joints of the fingers and hands were flexed in the typical triangular pattern. The skin was thick and leathery and substantially rigid.

Results: The patient's range of joint motion was measured prior to treatment and at periodic intervals during the treatment. This was done using the conventional passive range of motion test—passive. In general, the patient's range of joint motion began to improve within a few weeks after treatment had begun. The measurements achieved with the range of motion test are set forth in Table I below. The range of motion results After approximately seven months treatment the patient displayed improved range of joint motion and some reduction in skin thickness. An improvement in skin turgor was also apparent.

Patient No. 2—50 year old male

Diagnosis: Scleroderma with loss of muscle mass in chest and arms. On initial examination rales were evident with very little excursion on breathing.

Dosage: 9 grams per day of cartilage powder prepared according to Example II of the present invention for three weeks and thereafter 18 grams per day (375 gm—hard shell capsules); duration of treatment—8 months.

Results: The patient displayed excellent improvement in breathing and eventual disappearance of rales. Substantially improved lung capacity was noted with loss of "shortness of breath" symptoms. This patient's pulmonary function was measured using conventional spirametry and lung volume apparatus. The results of these tests are presented in Table II.

TABLE II

| LUNG VOLUMES | 10/26/81 | | 4/2/82 | |
|---|---|---|---|---|
| | OBSERVED | % PREDICTED NORMAL | OBSERVED | % PREDICTED NORMAL |
| FRC | 1.70 | 66 | 2.20 | 86 |
| ERV | 0.60 | | 0.80 | |
| RV | 1.10 | 64 | 1.40 | 82 |
| TLC | 3.70 | 60 | 3.90 | 63 |
| RV/TLC | 29.70 | 110 | 35.90 | 133 |

TABLE II-continued

| LUNG VOLUMES | 10/26/81 OBSERVED | % PREDICTED NORMAL | 4/2/82 OBSERVED | % PREDICTED NORMAL |
|---|---|---|---|---|
| SPIROMETRY | | | | |
| VC | 2.50 | 58 | 2.40 | 56 |
| FVC | 2.55 | 59 | 2.5 | 58 |
| $FEV_{1.0}$ | 2.20 | 86 | 2.3 | 92 |
| MVV | 138 | 96 | 120 | 83 |
| FLOW-VOLUME RELATIONSHIPS | | | | |
| PEAK FLOW | 7.6 | 88 | 8.30 | 97 |
| VC | 2.6 | 60 | 2.5 | 58 |
| $V_{50}$ | 3.2 | 1.23 | 5.4 | 1.9 |
| $V_{25}$ | 1.1 | 0.42 | 2.2 | 0.88 |

The lung volumes (a measurement of the lung's stiffness and the degree of disease present) are most significant. An improvement in lung volume measurement is recognized as an improvement in the disease process. Spirometry (which involves effort by the patient) is a less accurate measurement of the state of the patient's disease. Flow volume relationships are the results of a combination of the anatomic disease state and the patient's effort.

What is claimed is:

1. A method of treating progressive systemic sclerosis in a patient afflicted with progressive systemic sclerosis which comprises orally administering to said patient an effective amount for treating progressive systemic sclerosis a finely divided cartilage extract.

2. The method of claim 1 wherein said effective amount comprises between about nine and about twenty grams of finely divided cartilage extract per day.

3. The method of claim 1 wherein said effective amount is delivered in divided dosages throughout the day.

4. The method of claim 2 which comprises administering said cartilage extract in a solid dosage form.

5. The method of claim 4 wherein said solid dosage form is a capsule.

6. The method of claim 4 wherein said solid dosage form is a tablet.

7. The method of claim 6 wherein said capsule contains between about 50 and 500 milligrams of said extract.

8. The method of claim 6 wherein said cartilage extract is acid-pepsin digested and derived from bovine trachea.

9. The method of claim 7 wherein said cartilage extract is derived from shark cartilage.

10. The method according to claim 7 wherein said capsule contains 375 milligrams of cartilage extract.

11. The method of claim 4 which comprises administering said cartilage extract orally in the form of a solution, or suspension.

12. A method of improving joint mobility in a mammal affected with progressive systemic sclerosis which comprises orally administering to said mammal afflicted with said progressive systemic sclerosis an effective amount for improving joint mobility of an extract derived from granulated cartilage.

13. A method of alleviating skin tension in mammals afflicted with progressive systemic sclerosis with comprises orally administering to said mammals an effective amount for alleviating skin tension in a mammal afflicted with progressive systemic sclerosis of a cartilage product derived from granulated animal, reptile or fish cartilage.

14. The method of claim 13 wherein said effective amount comprises between approximately 9–60 grams of said cartilage product.

* * * * *